US00PP34520P3

(12) United States Plant Patent
Mostert

(10) Patent No.: US PP34,520 P3
(45) Date of Patent: Aug. 23, 2022

(54) ***PILEA* PLANT NAMED 'MOSPILMOJ'**

(50) Latin Name: *Pilea peperomioides*
Varietal Denomination: MOSPILMOJ

(71) Applicant: Beheer B.V., Nieuwerkerk aan den IJssel (NL)

(72) Inventor: Frederik Hendrik Mostert, Nieuwerkerk aan den Ijssel (NL)

(73) Assignee: KMN Beheer B.V., Nieuwerkerk aan den IJssel (NL)

( * ) Notice: Subject to any disclaimer, the term of this patent is extended or adjusted under 35 U.S.C. 154(b) by 0 days.

(21) Appl. No.: 17/347,047

(22) Filed: Jun. 14, 2021

(65) Prior Publication Data

US 2021/0392804 P1 Dec. 16, 2021

(30) Foreign Application Priority Data

Jun. 12, 2020 (QZ) ..... 2020/1425

(51) Int. Cl.
*A01H 5/00* (2018.01)
*A01H 6/84* (2018.01)

(52) U.S. Cl.
USPC ..... Plt./373
CPC ..... *A01H 6/84* (2018.05)

(58) Field of Classification Search
USPC ..... Plt./373
CPC ..... A01H 5/00
See application file for complete search history.

*Primary Examiner* — Kent L Bell
(74) *Attorney, Agent, or Firm* — Samuel R. McCoy, Jr.

(57) ABSTRACT

'MOSPILMOJ' is a distinctive *Pilea* plant which is characterized by the combination of a broad spreading to upright habit, variegated orbicular foliage with long petioles borne on a short main stem, green to yellow-green juvenile foliage that is mottled with a very light shade of yellow-green generally appearing as a yellowish coloration, green mature foliage that is conspicuously mottled with a light shade of yellow-green generally appearing as a very light green coloration, and the stability of all characteristics from generation to generation.

3 Drawing Sheets

Latin name of the genus and species: The Latin name of the genus and species of the novel variety disclosed herein is *Pilea peperomioides*.

Variety denomination: The inventive variety of *Pilea* disclosed herein has been given the variety denomination 'MOSPILMOJ'.

CROSS REFERENCE TO RELATED APPLICATIONS

This application claims priority to the Community Plant Variety Rights application is herein number 2020/1425, filed Jun. 12, 2020 which incorporated by reference.

BACKGROUND OF THE INVENTION

Parentage: 'MOSPILMOJ' originated as a naturally occurring, branch mutation of an unnamed *Pilea peperomioides* plant (not patented). In June of 2019, the inventor discovered the mutation at his commercial greenhouse in Nieuwerkerk aan den IJssel, The Netherlands on an unnamed *Pilea peperomioides* plant, growing amongst a cultivated population of unnamed *Pilea peperomioides* plants. The mutation was noted for its unique leaf variegation. The mutation was harvested from the mother plant by removing the portion of rhizome bearing the variegated foliage. The resulting rhizome cuttings, which each showed some slight variation in the leaf variegation pattern and color, were each re-rooted in individual nursery containers. These new plants were then grown to a mature size in order to select one plant from all other progeny that exhibited the optimal variegation pattern and color. In June of 2020, the inventor selected one of said variegated plants which he deemed to exhibit the optimal variegation pattern and color. Upon further confirmation of stability, 'MOSPILMOJ' was selected for commercialization.

Asexual Reproduction: Asexual reproduction of 'MOSPILMOJ', by way of meristematic tissue culture, was first initiated in the summer of 2020 at a commercial greenhouse in Nieuwerkerk aan den Ussel, The Netherlands. Through greater than 50 subsequent generations, the unique features of this cultivar have proven to be stable and true to type.

SUMMARY OF THE INVENTION

The cultivar 'MOSPILMOJ' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MOSPILMOJ'. These characteristics in combination distinguish 'MOSPILMOJ' as a new and distinct *Pilea* cultivar:

1. *Pilea* 'MOSPILMOJ' exhibits a broad, spreading to upright growth habit; and
2. *Pilea* 'MOSPILMOJ' exhibits variegated orbicular foliage, with long petioles, borne on a short main stem; and
3. *Pilea* 'MOSPILMOJ' exhibits green to yellow-green juvenile foliage that is mottled with a very light shade of yellow-green, generally appearing as a yellowish coloration; and 4. *Pilea* 'MOSPILMOJ' exhibits green mature foliage that is conspicuously mottled with a light shade of yellow-green, generally appearing as a very light green coloration.

BOTANICAL DESCRIPTION OF THE PLANT

Figure 1:
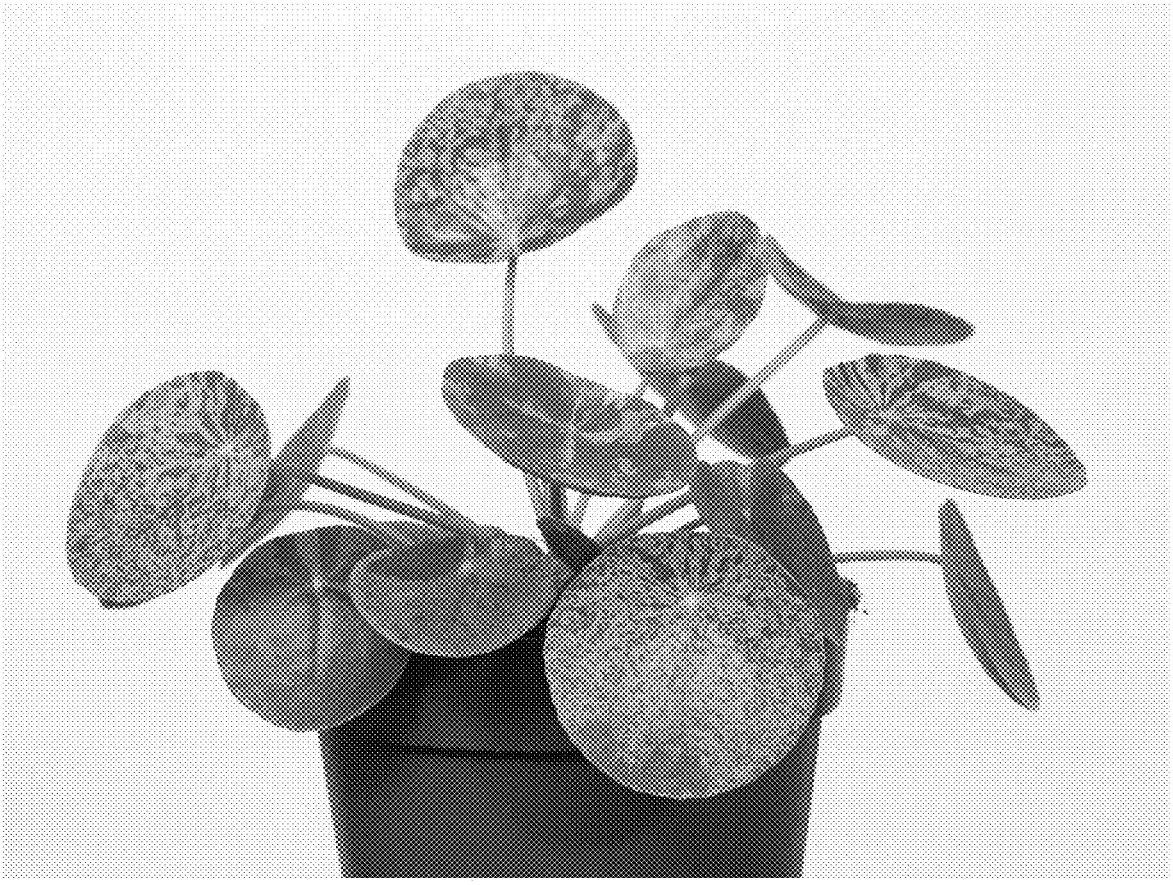
FIG. 1 illustrates, as nearly true as it is reasonably possible to make the same in color photographs of this type, two exemplary plants of 'MOSPILMOJ' grown in a commercial greenhouse in Nieuwerkerk aan den IJssel, the Netherlands. These plants are approximately 12 weeks old, shown planted in a 12 cm container.
Figure 2:
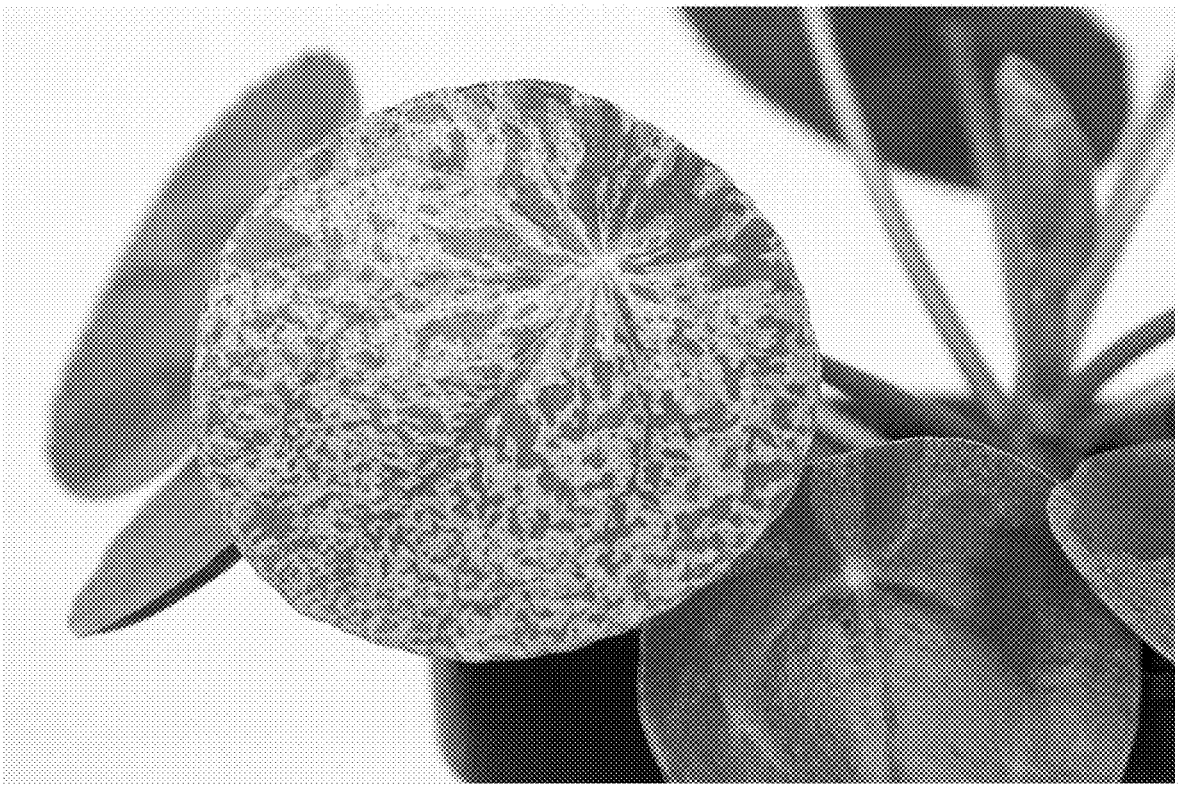
FIG. 2 illustrates, as nearly true as it is reasonably possible to make the same in color photographs of this type, the adaxial surface of the mature foliage of 'MOSPILMOJ'.
Figure 3:
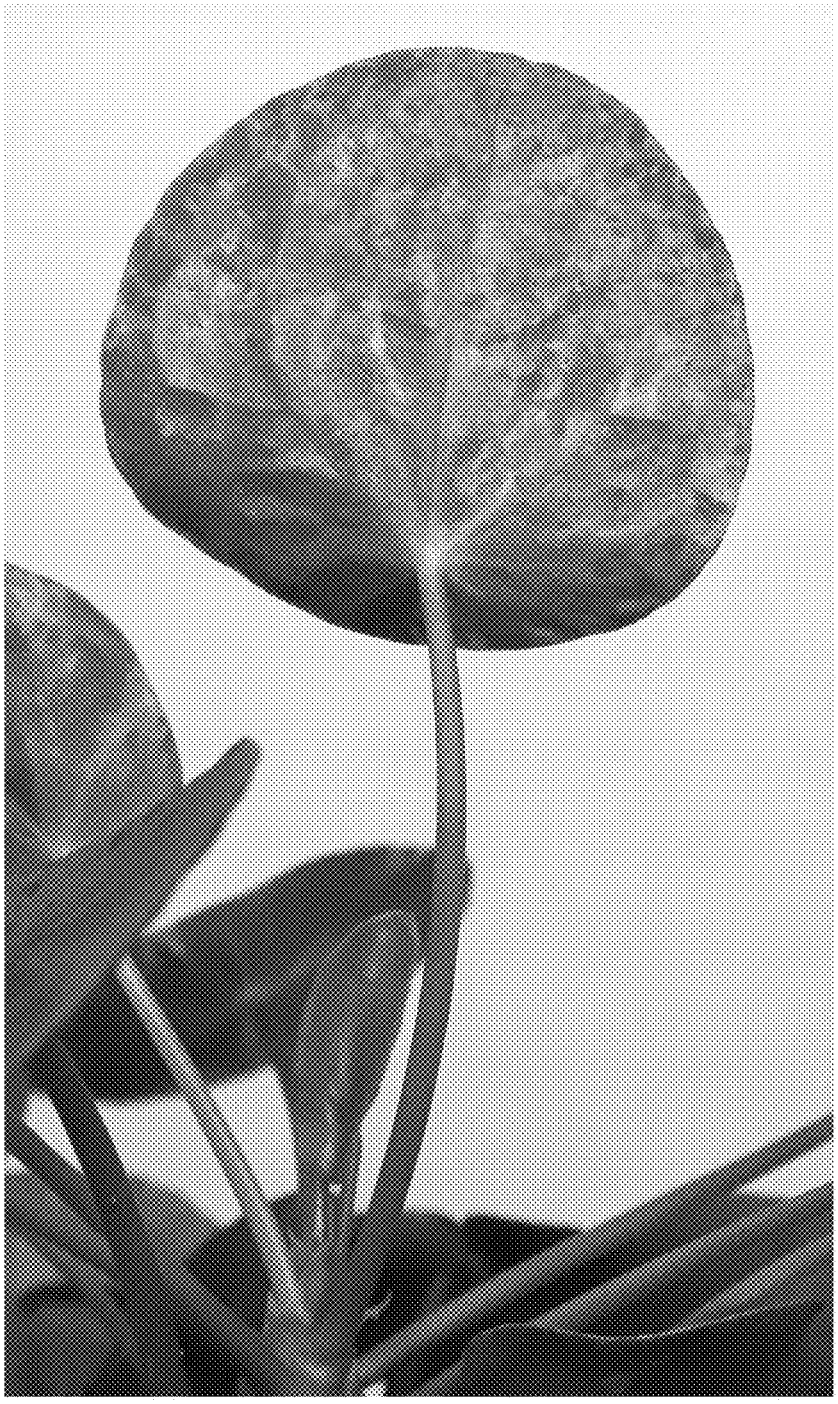
FIG. 3 illustrates, as nearly true as it is reasonably possible to make the same in color photographs of this type, the abaxial surface of the mature foliage of 'MOSPILMOJ'.

The following observations and measurements made in February of 2021 describe averages from two 12 week-old 'MOSPILMOJ' plants grown in a 12 cm nursery container at a greenhouse in Nieuwerkerk aan den IJssel, the Netherlands. Plants were produced in a greenhouse, using conventional greenhouse production protocols for *Pilea* plants. The ambient temperature of the greenhouse was held at a constant 20 degrees Celsius, and plants were grown under light shade (approximately 110 μmol/m2/s), as too much shade will affect the leaf color expression. Irrigation was supplied using ebb and flood tables and plants were fertilized with a 0.5 EC nutrient solution containing a micronutrients. Beneficial predatory insects were released on a weekly basis during production and chemical pest control measures utilized as needed.

Those skilled in the art will appreciate that certain characteristics will vary with older or, conversely, with younger plants. 'MOSPILMOJ' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'MOSPILMOJ' and a comparison with the parent plant and most similar commercial comparator are provided below.

Plant description:

*Growth habit.*—Herbaceous perennial with a broad, spreading to upright growth habit; leaves growing from a short stem.

*Plant shape.*—Broad obovate.

*Height from soil level to top of foliar plane.*—10.7 cm.

*Plant spread.*—22.6 cm.

*Growth rate.*—Moderately fast.

*Plant vigor.*—Moderately vigorous.

*Propagation type.*—Stem cuttings.

*Time to produce a rooted cutting.*—Approximately 21 days to produce a rooted cutting at approximately 20 to 21 degrees Celsius.

*Time to produce a finished plant.*—Approximately 11 to 15 weeks to produce a marketable finished plant in a 12 cm pot.

*Disease and pest resistance or susceptibility.*—Neither susceptibility nor resistance to pests and diseases common to *Pilea* sp. have been observed.

*Environmental tolerances.*—Adapt to temperatures as high as 40 degrees Celsius; moderately tolerant of rain and wind.

Roots:

*General.*—Sparse to moderately dense, moderately branched root system; fleshy rhizomes give rise to smaller fleshy roots.

*Distribution in the soil profile.*—Shallow to moderately deep.

*Texture.*—Smooth; no root hairs.

Stems:

*Branching habit.*—A single main stem arises directly from the soil.

*Number of main shoots per plant.*—1.

*Number of lateral branches per plant.*—0.

*Length of main shoot.*—3.7 cm.

*Diameter of main shoot.*—0.8 cm.

*Internode length on main shoot.*—0.5 cm.

*Attitude.*—Erect.

*Aspect.*—Rounded.

*Strength.*—Moderately strong.

*Texture and luster.*—Glabrous, smooth and matte.

*Color, juvenile.*—Yellow-green, nearest to RHS 152B.

*Color, mature.*—Greyed-red, nearest to RHS 178A.

*Color at internodes.*—Greyed-red, nearest to RHS 178A.

Foliage:

*Quantity.*—17 leaves per plant, as observed.

*Arrangement.*—Alternate.

*Attachment.*—Petiolate.

*Division.*—Simple.

*Lamina.*—Attitude — Nearly 90 degrees to the petiole. Shape — Orbicular. Length — 6.8 cm, excluding the petiole. Width — 6.9 cm. Apex — Rounded. Base — Rounded, yet slightly more blunt by comparison to the apex. Aspect — Slightly concave. Margins — Very slightly crenate; not undulated. Texture and luster, adaxial surface — Smooth, glabrous, and moderately glossy. Texture and luster, abaxial surface — Smooth, glabrous, and slightly glossy. Color — Juvenile foliage, adaxial surface — Nearest to in between green and yellow-green, RHS 143C and 144A; irregularly mottled with a lighter shade of yellow-green, nearest to a mixture of RHS 145B and 145C. Juvenile foliage, abaxial surface — Yellow-green, nearest to RHS 144A; irregularly mottled with a lighter shade of yellow-green, nearest to RHS 145B. Mature foliage, adaxial surface — Green, nearest to RHS 137B, with conspicuous yellow-green mottling; nearest to a mixture of RHS 144C, 146D, 147B and 147C. Mature foliage, abaxial surface — Yellow-green, nearest to a mixture of RHS 146A and 146B, with conspicuous yellow-green mottling; nearest to a mixture of RHS 144B, 145A, and 146D. Venation — Pattern — Laciniate. Color, adaxial surfaces — Veins are the same color as the surrounding foliar surface: Green, nearest to RHS 137B, with conspicuous yellow-green mottling; nearest to a mixture of RHS 144C, 146D, 147B and 147C. Color, abaxial surface — Yellow-green, nearest to RHS 146C.

*Petiole*.—Attitude — Upright and slightly outward. Strength — Somewhat weak to moderately strong. Length — 9.3 cm. Diameter — 0.3 cm. Texture and luster, adaxial surface — Smooth, glabrous and slightly glossy. Texture and luster, abaxial surface — Smooth, glabrous and slightly glossy. Color, adaxial surface — Greyed-orange, nearest to a mixture of RHS 177B and 177C. Color, abaxial surface — Yellow-green, nearest to a mixture of RHS 146C and 146D, and lightly suffused with a yellow coloration, nearest to RHS 152D.

*Stipule*.—Shape — Deltoid. Length — 0.9 cm. Width — 1.2 cm. Margin — Entire; not undulated. Texture and luster — Smooth, glabrous and slightly glossy. Color, adaxial and abaxial surfaces — Greyed-white, nearest to a mixture of RHS 159B and 159C, with a broad main vein colored greyed-orange, nearest to RHS 170D.

Inflorescence: To date, 'MOSPILMOJ' has not flowered.

COMPARISONS WITH THE PARENT PLANTS

Plants of the new cultivar 'MOSPILMOJ' differ from the parent, an unnamed *Pilea peperomioides* plant (not patented), in the characteristics described in Table 1 below.

TABLE 1

| Characteristic | 'MOSPILMOJ' | The parent |
|---|---|---|
| General coloration of the mature adaxial foliage surface; expression of variegation, | Green and conspicuously mottled with a light shade of yellow-green, generally appearing as a very light green coloration. | Green; no variegation present. |

COMPARISONS WITH THE CLOSEST KNOWN COMPARATOR

Plants of the new cultivar 'MOSPILMOJ' differ from the closest known commercial comparator, *Pilea peperomioides* 'White Splash' (Community Plant Variety Rights application number 2019/3122), in the following characteristics described in Table 2 below.

TABLE 2

| Characteristic | 'MOSPILMOJ' | 'White Splash' |
|---|---|---|
| General coloration of the mature adaxial foliage surface | Green and conspicuously mottled with a light shade of yellow-green, generally appearing as a very light green coloration. | Green and conspicuously mottled with a white coloration. |
| Expression of variegation. | Conspicuous; abundant. | Less prominent; less abundant. |
| Environmental influence on foliage color, | Lower light levels will turn the mottling from a yellowish coloration to a very light green coloration. | No environmental effect on variegation. |

That which is claimed is:

1. A new and distinct variety of *Pilea* plant named 'MOSPILMOJ', substantially as described and illustrated herein.

* * * * *